United States Patent [19]
Jaffrin et al.

[11] Patent Number: 4,578,191
[45] Date of Patent: Mar. 25, 1986

[54] BIO-ARTIFICIAL ULTRAFILTRATION PANCREAS

[75] Inventors: Michel Jaffrin, Compiegne; Gerârd Reach, Paris, both of France

[73] Assignee: Centre National de la Recherche Scientifique, Paris, France

[21] Appl. No.: 519,315

[22] Filed: Aug. 1, 1983

[30] Foreign Application Priority Data

Aug. 9, 1982 [FR] France .................. 82 13869

[51] Int. Cl.⁴ .................................. B01D 13/00
[52] U.S. Cl. ........................... 210/323.2; 210/433.2
[58] Field of Search ............ 210/321.4, 321.1, 456, 210/632, 433.2, 638, 648, 363.2; 3/1; 435/284

[56] References Cited

U.S. PATENT DOCUMENTS

| | | | |
|---|---|---|---|
| 3,585,131 | 6/1971 | Edmund | 210/321.4 |
| 3,660,281 | 5/1972 | Tuber | 210/321.1 X |
| 3,827,565 | 8/1974 | Matsumura | 210/632 |
| 3,900,398 | 8/1975 | Gillette | 210/456 X |
| 4,025,436 | 5/1977 | Tsuda et al. | 210/321.3 |
| 4,038,190 | 7/1977 | Baudet et al. | 210/321.3 |
| 4,048,064 | 9/1977 | Clark, III | 210/638 |
| 4,242,460 | 12/1980 | Chick et al. | 210/321.1 X |
| 4,276,175 | 6/1981 | Bower | 210/648 X |
| 4,323,457 | 4/1982 | Sun et al. | 210/321.1 X |
| 4,361,484 | 11/1982 | Larsson et al. | 210/632 |
| 4,401,566 | 8/1983 | Igari et al. | 210/433.2 X |

Primary Examiner—Frank Spear
Attorney, Agent, or Firm—Larson and Taylor

[57] ABSTRACT

The bio-artifical pancreas comprises islands of Langerhans contained in a volume defined by two approximately parallel ultrafiltration membranes, able to be formed by two successive portions of the same flat membrane or the same hollow fiber. The surfaces of the membrane opposite the volume occupied by the islands are successively swept by the same blood stream over a length greater by at least one order of size than the distance separating the membranes.

10 Claims, 9 Drawing Figures

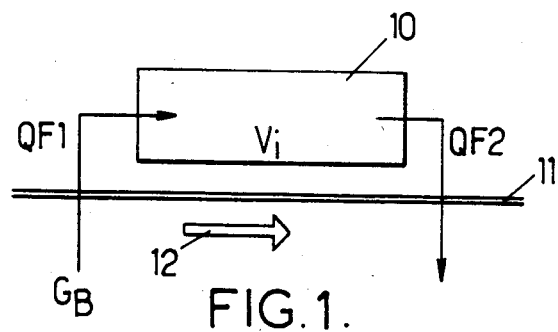
FIG.1.
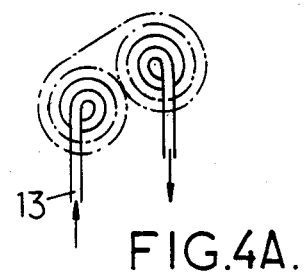
FIG.4A.
FIG.4B.
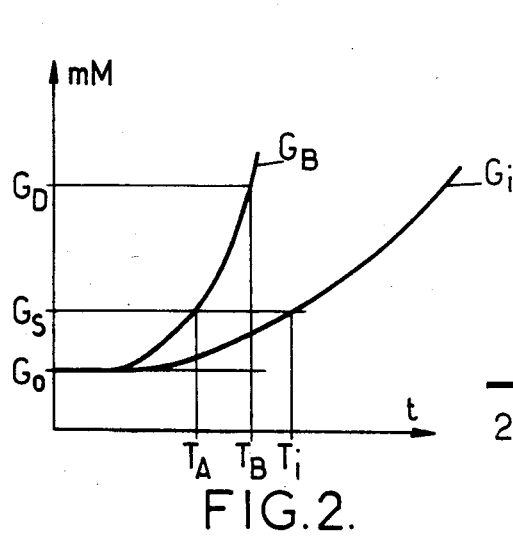
FIG.2.
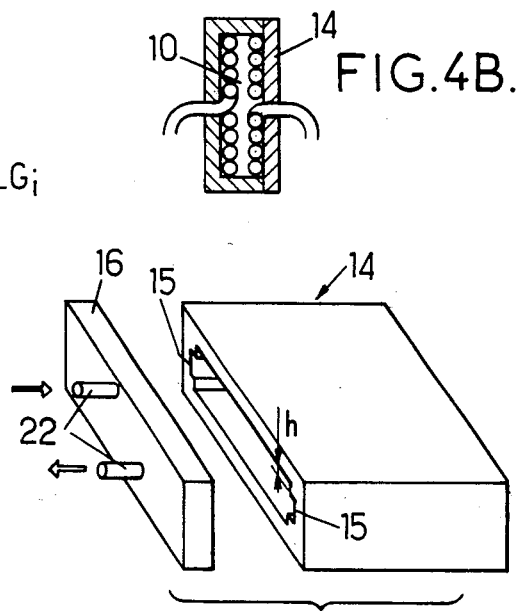
FIG.5.
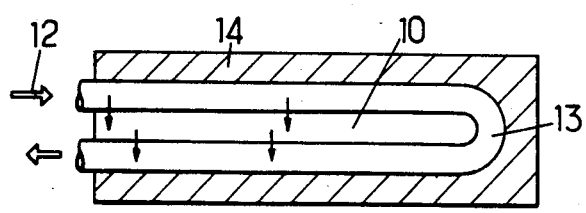
FIG.3.
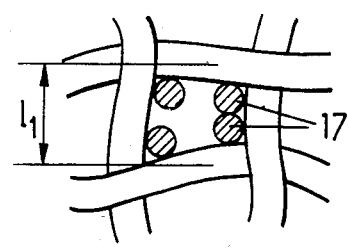
FIG.6.

BIO-ARTIFICIAL ULTRAFILTRATION PANCREAS

FIELD OF THE INVENTION

The invention relates to a bio-artificial pancreas, i.e. a device for regulating the glycemia of a diabetic subject. The device comprises islets of Langerhans (possibly from a being of another nature than the carrier of the pancreas) for secreting the insulin and protecting against immuno-rejection by a membrane permeable to glucose and insulin but impermeable to immunoglobulins and immunocytes.

BACKGROUND AND SUMMARY OF THE INVENTION

A bio-artificial pancreas, which will be designated hereafter by the abbreviation PBA, is more effective when its response to a concentration variation of the glucose in the blood is closer to that of the biological pancreas. Insulin must be secreted by the islets and reach the blood stream before the glycemia reaches an acceptable maximum, however much the slope of the curve of glycemia increase differs from the normal rate.

Numerous studies have already been made for providing a PBA having acceptable kinetics. A summary of these studies may be found in a paper by G. REACH et al in "Journées Annuelles de Diabétologie de l'Hôtel-Dieu", Flammarion, Paris, 1982, pp 147 to 159.

In all devices, the operating principle is the same: the islets of Langerhans are separated from the diabetic host by an artificial bio-compatible membrane permeable to glucose and insulin. Two types of transfer of the glucose to the islets of Langerhans causing excitation of the latter have been proposed which lead to membranes of two different natures.

A first type of membrane uses diffusion, i.e. the passage of the liquid solution through the membrane. This amounts to dialysis, which is not satisfactory, for it requires a concentration gradient, which delays the stimulation of the islets of Langerhans and takes place at different speeds for glucose and insulin. This has a detrimental effect on the transfer function of the regulation process between the glycemic variations and the delivery of insulin into the blood.

Another type of membrane operates mainly due to convection—also known as ultrafiltration—i.e. the passage through the membrane of the solvent which takes with it the substances dissolved therein. Ultrafiltration membranes are usable for this type of transfer; they retain the heaviest molecules. No concentration gradient is required, which is a favorable factor, and the transfer speed is determined by the hydrostatic pressure gradient through the membrane and its hydraulic permeablility.

Attempts have already been made to construct a PBA using a ultrafiltration membrane. A PBA is known (U.S. Pat. No. 4,242,460 to Chick et al.) in which the cells are disposed between the jointing turns of helices through which the blood flows in reverse directions and contained in a cylindrical case. With this double helix arrangement only a small fraction of the filtering membranes in the form of a helix is used (that which borders the narrow canals defined by two adjacent turns) and the convective current only flows through a small part of the volume in which the islets are placed. The islets which are not in this part remain unused.

Moreover, some PBAs which have a satisfactory response when a sudden increase of the glycemia occurs (obtained for example during tests by intravenous injection) do not allow the glycemia to be maintained below the tolerable limit in the case of a slow variation, e.g. following a meal.

It is an object of the invention to overcome that drawback and to provide a PBA which has (1) an improved response and allows the glycemia to be held at an acceptable rate whatever its law of variations in time; (2) uses the major part of the filtering area and most of the islets used; and (3) allows the arterial pressure alone to be used for the production of the ultrafiltrate, to the exclusion of any exogenous pump.

This result has been reached because of a fundamental approach to the phenomena which come into play, an approach which has led to the discovery that an essential parameter for determining the functional characteristics is the volume of the compartment containing the islands. Taking this analysis into account, the invention proposes a PBA comprising islands of Langerhans contained in a volume defined by two approximately parallel ultrafiltrating walls-which will be designated hereafter by the term "membranes" whose surfaces opposite the volume occupied by the islands are successively swept by the same blood stream over a length greater by at least one order of size than the distance which separates the membranes.

Such a PBA, where the islands occupy a flat volume, may be constructed with membranes of very different natures. Flat membranes may in particular be used, made for example from polyacrylonitrile such as the ones sold under the reference "AN 69" by RHONE POULENC. A web of hollow ultrafiltrating fibers may also be used. The geometric arrangements adoptable are also very diverse, as will be seen further on.

In practice, the volume $V_i$ occupied by the islands of Langerhans and defined by the membranes will comply with the condition:

$$V_i = S \cdot P_M \cdot \tau \Delta P / 8$$

in which:

$\tau$ is the acceptable time constant, and physiological studies thereof carried out on man indicate that it should not exceed 20 minutes and should, preferably, be 15 minutes at most;

$\Delta P$ is the available drive pressure difference, of the order of 80 mm of mercury in the general case of an ateriovenous shunt implant;

S is the total membrane area;

$P_M$ is the hydraulic permeability of the membrane.

The invention will be better understood from the detailed description of particular embodiments.

SHORT DESCRIPTION OF THE DRAWINGS

FIG. 1 is a diagram showing the principle of construction of a bio-artificial pancreas and the magnitudes which play a part in its operation;

FIG. 2 gives the curves representative of glycemia $G_B$ in the blood and of the glucose $G_i$ concentration in the compartment containing the islands of a PBA, as a function of time, in response to sugar absorption;

FIG. 3 is a simplified diagram showing a hollow fiber PBA;

FIGS. 4A and 4B show the arrangement of a fiber in a variant;

FIG. 5 shows a PBA case with flat membrane;

FIG. 6 is a schematical detail view showing the positioning of the islands of Langerhans in a lattice;

DETAILED DESCRIPTION OF PARTICULAR EMBODIMENTS

Figure 7:
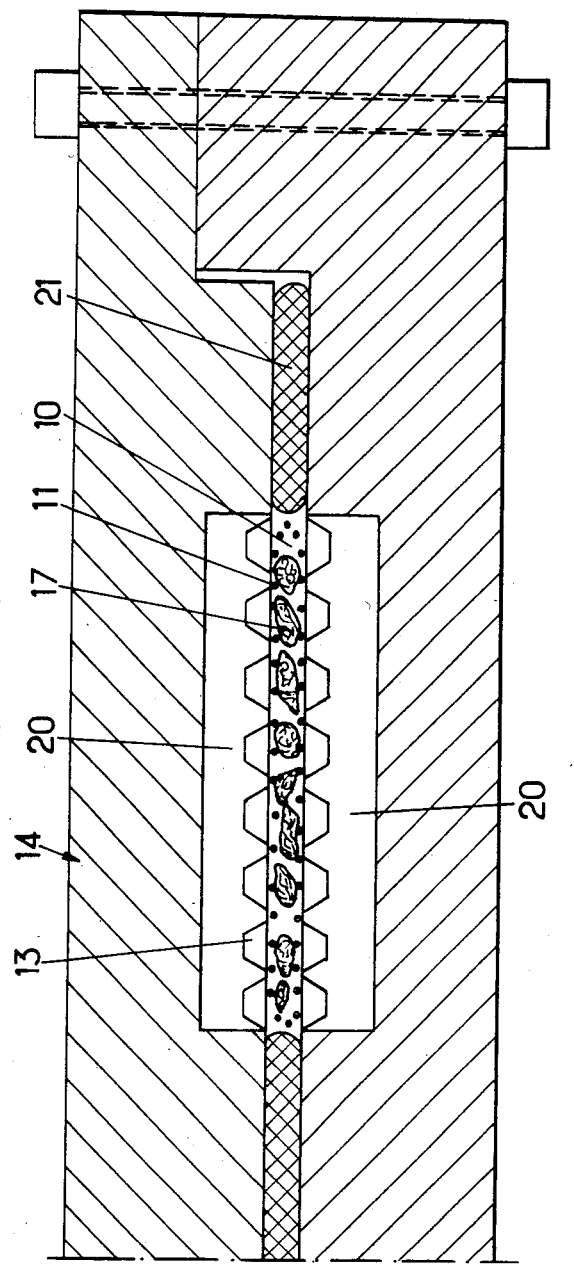
FIG. 7 shows yet another variant using two ultrafiltration membranes, in a section through a plane perpendicular to the flow direction of the blood stream.

It may be worthwhile to point out some of the operations which a PBA must carry out, and to give an analysis of a PBA model.

The principle of a PBA is the following: a pancreatic tissue is placed in a compartment 10 separated by an ultrafiltration membrane 11 from the blood stream of the diabetic host, which stream is shown schematically by an arrow 12. The membrane has passing therethrough an ultrafiltrate flow QF1 in the blood-islands direction and, in its downstream part, an ultrafiltrate flow QF2 in the islands-blood direction. The value $V_i/QF1$ ($V_i$ being the volume of the compartment 10) will be called the time constant $\tau$. It will be seen that this time constant corresponds to the delay of insulino-secretion by the PBA, with respect to a normal endocrine pancreas, for very slow variations of the glycemia $G_B$, for example following a meal. Following an injection of glycemia, $G_B$ and $G_i$ rise, in accordance with a law of the kind shown in FIG. 2, from the glycemia $G_O$ on an empty stomach. The islands of Langerhans begin to secrete the insulin as soon as the glycemia reaches an insulino-secretion threshold $G_s$. In the case of the biological pancreas, the secretion begins at time $T_A$ for which $G_B=G_S$. In the case of a PBA, the secretion begins at time $T_i$ for which $G_i=G_S$. If we designate by $T_B$ the time at which the glycemia reaches the upper acceptable limit $G_D$, a condition required for the PBA to be efficient is that we have:

$$T_i \leq T_B$$

It is only in this case that the PBA ensures administration of insulin, regulated by the glycemia, with a delay sufficiently small to maintain it within acceptable limits.

Account must moreover be taken not only of the insulino-secretion delay, which only occurs once the glucose concentration in compartment 10 has reached a threshold $G_S$, but also of the time required for the mass transfer of the insulin secreted through the membrane 11. It will be seen that, in a PBA of the invention, the short length of the path followed by the flow QF2, associated with the favorable characteristics of the ultrafiltration membrane 11, allows the time required for the mass transfer to be neglected.

Using the model of FIG. 1, the relationship which exists between the speed $\alpha$ of variation of glycemia in the blood, the time constant $\tau$ already defined and the delay $R=T_B-T_A$ in insulino-secretion may be determined by calculation. We find the relationship to be:

$$\tau\left[\exp\left(\frac{R+G_s-G_O}{\alpha\tau}\right)-1\right]+R+O$$

Examination of this formula shows that R tends towards $\tau$ when $\alpha$ tends towards 0, i.e. $\tau$ is the delay in insulino-secretion by the PBA, with respect to the normal pancreas, for slow variations of the glycemia. This formula also shows that R depends largely on $\alpha$ and that, for a PBA to be satisfactory, R must remain acceptable even in the most unfavorable case where $\alpha$ is low. Incidentally, the formula shows why different prior PBAs improve the tolerance to glucose administered venously, whereas they are inefficient to combat the increase in glycemia following a meal. In the first case, $\alpha$ is very large and we arrive at a delay R not exceeding ten minutes. On the contrary, in the case of a meal, $\alpha$ is low and we arrive at a value of R exceeding forty minutes. Now, experience of open or closed loop (i.e. with regulation) insulino therapy shows that the delay R should not exceed twenty minutes and should advantageously remain less than or equal to fifteen minutes. Consequently, a PBA complying with the model described above will have to fulfil the condition:

$$V_i/QF1 < 20 \text{ min (and preferably 15 min)}$$

This condition requires a low volume for compartment 10. This result can only be reached by adopting different geometrical arrangements from those proposed up to now. More precisely, the islands of Langerhans must be disposed in a thin volume, defined by two approximately parallel ultrafiltrating membranes swept on their outer surfaces by the same blood stream. The pressure in this blood stream decreases along the travel path because of the distributed pressure loss which it undergoes. In a first portion of the path, where the pressure of the blood stream will be greater than the pressure in compartment 10 occupied by the islands, the flow QF1 will pass through the filtrating membrane. In the second portion, where the blood pressure is less than the pressure in the compartment, the flow QF2 and the mass transfer of the insulin will pass to the blood stream.

The two ultrafiltrating membranes will generally be formed by two successive portions of the same membrane bent in a U on itself. This membrane may be either flat, or formed by one or more hollow fibers with an internal diameter sufficient to avoid coagulation.

The diagram of FIG. 3 shows the principle of construction of a PBA with a single fiber 13 bent into a hairpin shape through which flows a blood stream. The fiber is placed in a case 14 and defines the volume 10 occupied by the islands. Because of the reduction of the hydrostatic pressure following the pressure drop along the flowpath, the ultrafiltration flowrate per unit of length in compartment 10 decreases from the inlet to a given distance $L_1$, substantially equal to half the total length L of the fiber, where it is cancelled out. Beyond, there is reversal of the ultrafiltration flow and a progressive increase of the linear ultrafiltration flow as far as the outlet.

A theoretical study of this principle of construction shows that the regulation prevents a hyperglycemia from exceeding the threshold $G_B$ if the following condition is fulfilled:

$$V_i \leq \frac{S \cdot P_M \cdot \tau \cdot \Delta p}{8} \quad (1)$$

In this formula, $\tau$, $\Delta p$ and $P_M$ have the above indicated meaning. Surface S to be taken into consideration is obviously only that which defines compartment 10.

Thus, for a given membrane area, with hydraulic permeability $P_m$, there exists a maximum volume of compartment 10 for keeping an acceptable value of τ, typically 15 mins., when the PBA forms an arteriovenous shunt, for which Δp is determined to be about 80 mm of mercury. The volume may be greater the higher the permeability. By way of example, in the case of an implant in a rat using an AMICON XM50 membrane 50 cm long and 0.4 mm in radius (below which there is a risk of coagulation), the volume $V_i$ should not exceed 200 μl. The flow which then passes through the PBA is compatible with the shunt from the carotid in the rat.

It should be noted in passing that, because of the hairpin structure of the fiber, the return time of the ultrafiltrate is very short. If the two legs of the fiber are separated by a distance corresponding to the thickness of an island, i.e. 200 μm and if 0.008 μl are formed on average per minute in the compartment, the mass transfer takes place on average within one minute, which is neglible with respect to the transmission time of the variation in the glucose rate.

A simple hairpin structure has the drawback of an excessive length for implant purposes. Different solutions allow this difficulty to be overcome and at the same time reduce the problems of curvature of the fiber in a small radius. As shown in FIGS. 4A and 4B, the fiber 13 is coiled to form two successive snails which are then applied against each other while leaving simply enough thickness for inserting the islands, in a case 14 of flat shape. With twice seven turns, a compartment 10 may be formed having a volume of the order of 100 μl, able to receive 800 islands 250 μm in diameter. However, we meet in this construction problem of small radius curvatures when the internal turn is of a small diameter. The problem is totally overcome, at the price of a reduction in compactness, by using a double solenoid construction.

In another embodiment of the invention, a flat flexible membrane is used. In this case, the whole of the surface of the membrane is used for defining the compartment 10 in FIG. 3. With the islands 17 situated between the two legs of the membrane, a mechanical arrangement should be adopted for sliding the assembly of the islands and the membrane into case 14 (FIG. 5).

A convenient arrangement, which moreover reduces the volume $V_i$, consists in separating the sheets of the membrane by means of a synthetic thread lattice (polyamide or polyester in general) defining meshes where the islands are located.

A few examples of embodiments with dimensions given will now be presented.

Figure 8:
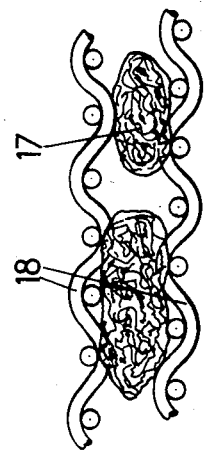
FIG. 8 is a detail view on a larger scale showing the bag of FIG. 7.

To construct a PBA usable for test on rats, a space occupancy, viewed from above, of 65×5.5 mm may be used, which defines a membrane area S of 7.15 cm². To allow an increased thickness e of compartment 10, a lattice of 300 μm in thickness is placed between the two legs of the membrane (FIG. 6). This lattice maintains moreover the spacing at a given value. If a membrane AN 69, manufactured by RHONE POULENC is used whose permeability $P_m$ is 25 ml/h/m²/mmHg, a lattice may be adopted with a pitch $l_1 = 0.5$ mm, each mesh receiving four islands. Another more advantageous solution can be found in using an AN 69S membrane having a permeability of 40 ml/h/m²/mmHg, with a lattice having a pitch of 1 mm. The 800 islands required may be positioned solely in the meshes of the first third of the lattice, where the difference in hydrostatic pressure between the two legs causes a considerable transmembrane flow. Since the overall pressure difference available on an arterio-venous shunt does not exceed 80 mm of mercury and since the connections result in pressure drops which may reach 10 mm of mercury, the average thickness of the blood film is approximately determined. For a flowrate of 5 ml/min, this thickness will be of the order of 200 μm. If this thickness is exceeded while maintaining the flow rate at the same value, there will be a lowering of the transmembrane flow and thus a lowering of efficiency. Another arrangement which has the great advantage of facilitating the positioning of the islands of Langerhans 17, is shown in FIGS. 7 and 8. The islands are placed in a cloth bag 18 formed of heat-weldable threads able to serve as a culture medium. A polyamide is preferably used. The meshes of the bag should have a dimension such that the islands cannot escape. A mesh less than 70 μm between 30 μm threads gives satisfactory results.

In the case shown in FIG. 7, the canals 13 through which the blood stream flows are defined by a polyacrylonitrile membrane 11 and grooves formed in pieces 20 supporting the membranes are held in a case 14 made in two parts assembled together. A reinforced silicon base elastomer seal 21 is inserted between the two parts of the case. The membrane is subjected to a pressure difference tending to move it away from the islets but is retained by the associated part 20. A thickness of compartment 10 may be about 360 μm and the groove depth may be about 400 μm. Several cases of this type may be assembled in parallel.

It should be further noted that the part of the membrane proximate the curved end of the U plays scarcely any role for the transfers, especially if compartment 10 does not contain any islands in this zone. The length of the lattice and of the membrane may then be reduced, as can the space occupied, seen from above, by the PBA, while locally increasing the pressure drop near the curved end of the U. This increase may be achieved by reducing the thickness of the blood film or its width at this position, for example by means of a constriction which must however be formed so as not to create risks of local coagulation and obturation.

Such a PBA may be fitted in a case of the kind shown in FIG. 5. The membrane is first of all laid flat, then covered over half of its length by the lattice. The islands of Langerhans are deposited in the meshes of the lattice, then the membrane is closed on the lattice. The assembly thus formed is then fitted into case 14, provided with lateral grooves 15 for guiding and holding the sandwich thus formed. Groove 15 has a thickness corresponding to that of the membrane and the lattice, and the distance h between the edges of the grooves and the bottom of the cavity in the case fix the thickness of the blood films. A lid, having sealing means not shown, then closes the case. Connections 22 provided in the lid allow the circulation to be organized.

When it is desired to extrapolate such a PBA to a human organism, account must be taken of the fact that the number of islands required reaches about 200,000. But the available arterio-venous pressure difference is not substantially modified although the blood flow which may be deviated may be increased, and practically multiplied by 15 in the case of an implant on the arm. The best solution seems then to be to dispose the islands in several layers while providing a thicker lattice or several superimposed lattices. Thus, construction of a flat membrane PBA may be contemplated occupying a space, seen from above, of 130×55 mm, which allows an acceptable length/width ratio to be kept. The membrane defines a blood film of 320 μm in thickness and a compartment between the two folds of the membrane contains four layers of islands distributed in the meshes of the lattice.

Other arrangements are further possible, for example in a coiled form, but they make the positioning in the case more difficult.

It goes without saying that the present invention is not limited to the particular embodiments given by way of examples, but extends to any variant remaining within the framework of equivalences.

We claim:

1. A bio-artificial pancreas comprising:
two ultrafiltration membranes having approximately parallel substantially planar confronting surfaces spaced apart a distance such that the space there between defines a volume of small thickness;
islets of Langerhans contained in said compartment;
means defining a blood path whereby blood flowing along said blood path successively sweeps said surfaces of said two membranes opposite said volume occupied by said islets of Langerhans over a length greater by at least one order of magnitude than the distance which separates said membranes;
said membranes being constructed and arranged such that said volume fulfills the condition;

$$V_i \leqq (S)(P_M)(\tau)(\Delta P/8)$$

in which
$V_i$ = said volume,
S = total membrane area,
$P_M$ = hydraulic permeability of membrane,
$\tau$ = acceptable time constant, and
$\Delta P$ = available drive pressure.

2. The bio-artificial pancreas according to claim 1, wherein said membranes are two successive portions of the same flat membrane folded in a U.

3. The bio-artificial pancreas according to claim 2 further comprising a lattice defining the thickness of said volume and reducing said volume, said lattice being located between said confronting surfaces.

4. The bio-artificial pancreas according to claim 3, wherein the islets of Langerhans are disposed in the openings of said lattice.

5. The bio-artificial pancreas according to claim 2, wherein said volume only contains islets of Langerhans in the part distant from the curved end of the U.

6. The bio-artificial pancreas according to claim 2, wherein the path of the blood stream presents a constriction for creating a pressure drop proximate the curved end of the U.

7. The bio-artificial pancreas according to claim 1, wherein said two ultrafiltration membranes comprise approximately parallel confronting walls of a U-shaped hollow ultrafiltrating fiber.

8. A bio-artificial pancreas according to claim 1 wherein said islets of Langerhans are located in a cloth bag accommodated in said volume.

9. A bio-artificial pancreas according to claim 1 further comprising a member for supporting said membranes and wherein said blood path comprises one or more grooves formed in said membrane supporting member.

10. A bio-artificial pancreas according to claim 1 wherein said ultrafiltration membranes comprise a hollow ultrafiltration fiber formed into two mutually parallel substantially planar sheets forming said confronting planar surfaces, said blood path defining means comprising said hollow ultrafiltration fiber.

* * * * *